United States Patent [19]

Nagasaka et al.

[11] Patent Number: 4,596,953
[45] Date of Patent: Jun. 24, 1986

[54] APPARATUS FOR SCANNING A MATERIAL FOR DETECTION OF FLAWS AND HAVING MATERIAL AXIS DEVIATION DETECTION

[75] Inventors: Hiroyasu Nagasaka, Chiryu; Masashi Mizuno; Katuhiro Kozima, both of Aichi, all of Japan

[73] Assignee: Daidotokushuko Kabushikikaisha, Japan

[21] Appl. No.: 484,830

[22] Filed: Apr. 14, 1983

[30] Foreign Application Priority Data

| Apr. 14, 1982 | [JP] | Japan | 57-62037 |
| Jul. 12, 1982 | [JP] | Japan | 57-120804 |
| Jan. 7, 1983 | [JP] | Japan | 58-1493 |

[51] Int. Cl.$^4$ ............ G01N 27/82; G01N 29/04; G01B 7/14
[52] U.S. Cl. .............................. 324/242; 73/622; 324/207; 324/226; 324/227; 324/262
[58] Field of Search ............ 324/207, 226, 227, 232, 324/242, 243, 261, 262; 73/618, 622, 633, 640, 661; 356/237

[56] References Cited

U.S. PATENT DOCUMENTS

| 3,746,972 | 7/1973 | Mandula, Jr. et al. | 324/262 X |
| 3,781,663 | 12/1973 | Abarotin et al. | 324/262 |
| 3,919,628 | 11/1975 | Mandula et al. | 324/261 |
| 3,955,425 | 5/1976 | Corneau | 73/622 |

*Primary Examiner*—Gerard R. Strecker
*Attorney, Agent, or Firm*—William A. Drucker

[57] ABSTRACT

Apparatus for detecting flaws on the circumference of a rounded bar of metal. A circular rotator means held by a support is rotated around the material to be inspected for flaws. The rotator means has a number of probes which are revolved around the circumference of the material to detect flaws when the rotator means is rotated. If and when the material deviates from its axis predetermined through the apparatus while passing therethrough, the deviation is detected and the support is displaced in the same direction and distance as the material so that the probes remain spaced apart from the circumference of the material at a predetermined distance while inspecting the material for flaws.

8 Claims, 17 Drawing Figures

APPARATUS FOR SCANNING A MATERIAL FOR DETECTION OF FLAWS AND HAVING MATERIAL AXIS DEVIATION DETECTION

BACKGROUND OF THE INVENTION

1. Field of the Invention

This invention relates to apparatus for detecting flaws on metal materials, and particularly to those with probes which are revolved around a bar of metal material so as to detect flaws on its circumference while the material is passed through the apparatus in its lengthwise direction.

2. Description of the Prior Art

When the foregoing technique is used to detect flaws, the probes are required to keep a constant distance from the circumference of the material, while revolving around the material, in order to ensure a higher degree of detection accuracy.

With reference to FIG. 17, the conventional detector of the type stated comprises a circular means 303 which is rotatable around a predetermined axis 302 of a material 301 to be passed through the detector and a cylinder 304 which is connected to the rotator means 303 and has a piston rod 304a provided with a probe 305 at its one end. In addition, the probe 305 is provided with a sensor means 306 which determines the distance between the probe 305 and the material 301. In such a constrction, if the material 301 happens to deviate from its predetermined axis 302 while passing the detector, the amount of deviation is detected by the sensor means 306 and the probe 305 is displaced by the cylinder 304 according to the detected amount of deviation so that the probe 305 keeps the unvaried distance from the material 301. To be more exact, the actual axis of the material may deviate from its predetermined one 302, or the rotational center of the rotator means 303, as indicated by numeral 307 (if the material is warped at a certain portion thereof) so that the material comes to the position indicated by a dot-dash-line; thereupon, in order to keep the constant distance, the probe 305 is withdrawn the same distance as the deviation of the material axis (the deviation distance hereafter called "L") while the probe 305 revolves 180° (immediately after the deviation has occurred), and then advanced the distance L while it revolves another 180°. That is, after the material axis has deviated, the probe 305 is removed by twice the distance L while it makes one revolution. In addition, the rotator means 303 may be rotated, for example, at a rate of several tens of revolutions per second; where such is the case, therefore, the probe 305 is required to keep reciprocating at an extremely-high velocity so as to cover the entire range of continuous deviation of the material axis, thus calling for an extremely-excellent degree of technique therefor.

SUMMARY OF THE INVENTION

It is an object of the invention to provide a flaw detector whereby a material is inspected for flaws with a constant distance maintained between the circumference of the material and probes.

Another object of the invention is to provide a flaw detector of the type stated whereby the distance between the circumference of the material and probes is not subjected to variation, but can be maintained constant even if the actual axis of the material has been deviated from its predetermined one by a warped portion thereof passing into an inspection or detection space.

A still another object of the invention is to provide a flaw detector having a relatively-simple construction to keep constant the distance between the circumference of the material and probes even in the event of deviation of the axis of the material from its predetermined one. According to the invention, if the material axis has deviated, the center of revolution of the probes can be instantly made re-coincident with the material axis simply by displacing a means supporting a rotator means in accordance with the amount of deviation of the material. In most cases, since the degree of its deviation caused by its warped portion is very small (of several millimeters, for example) compared with the length of the material, the degree of deviation per time for a unit length of the material to pass is very small; in other words, the material axis may deviate gradually. Hence the support means may be displaced slowly to compensate the deviation, thus requiring no complicated technique in order to keep constant the distance between the circumference of the material and the probes.

Other objects and advantages of the invention will become apparent during the following discussion of the accompanying drawings.

DESCRIPTION OF THE PREFERRED EMBODIMENTS

Figure 1:
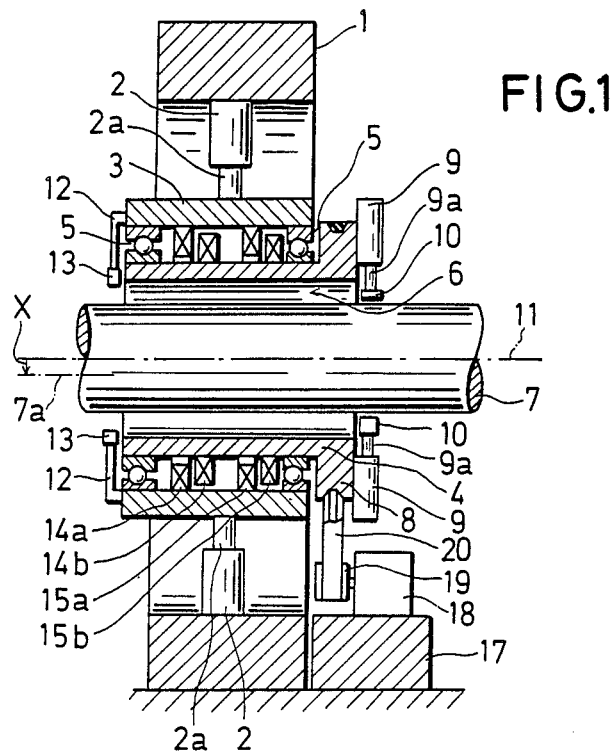
FIG. 1 is a vertical cross section of a first form of flaw-detector construction according to the invention.
Figure 2:
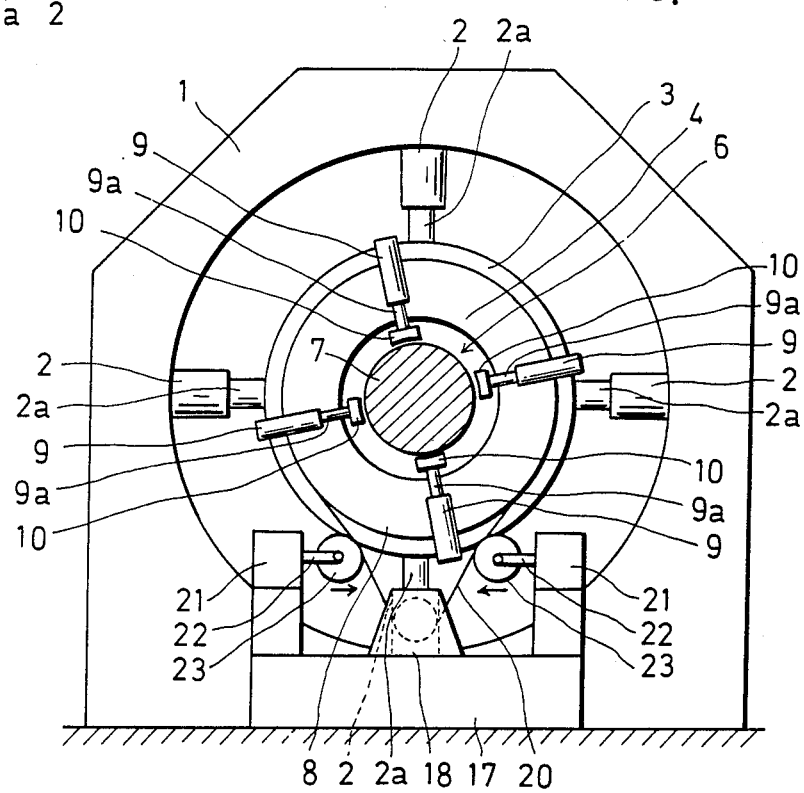
FIG. 2 is a side elevation (right-hand side) of the construction of FIG. 1.

Referring to FIGS. 1 and 2, one embodiment of the invention includes an annular framework 1. A plurality of cylinders 2 having piston rods 2a are connected to the inside of the framework 1 at one end thereof and in circular arrangement. A tubular support 3 is connected to the inner ends of the piston rods 2a. A rotator means 4 is movably (rotatably) connected to the support 3 through bearings 5. The rotator means 4 is also shaped into a tubular form, and has a cylindrical space 6 through which to pass a rounded bar 7 of metal or other kind of material to inspect it for flaws (breaks, scratches, cracks, etc.). For example, the material 7 may be one that has been passed through a heat-treatment device and is on its way to a rolling device, or that is still being subjected to repeated rolling operations, but happens to be outside the rolling device, or that has already been rolled and is on its way to a cutter.

One end of the rotator means 4 is projected outward to provide a pulley means 8. A plurality of cylinders 9 are connected to the pulley means 8 at one end thereof and in circular arrangement. The cylinders 9 each have a piston rod 9a with a free inner end to which is attached a probe 10 for detecting flaws on the surface or circumference of the material 7. In the particular embodiment herein, the probe 10 is one for the detection of flaws by eddy currents; however, it may be one for ultrasonic detection or for optical detection. A plurality of deviation sensors 13 are connected to the tubular support 3 by installation means 12. The function of each sensor 13 is to detect the axis of the material 7 deviating from a predetermined axis 11 (for passing the material through the cylindrical space 6) by measuring the distance between the sensor 13 and the circumference of the material 7. The sensor 13 may also be of an eddy-current type, of an optical type, or of any other suitable type. Each sensor 13 is located in conjunction or proximity with one of the cylinders 2. Between the sensor 13 and the cylinder 2 thus associated with each other is provided a means (not shown) for operating the cylinder 2 in accordance with the detection of deviation of the material 7 by the sensor 13. This operation means may be an electric or hydraulic one. A number of pairs of signal transmitters 14a, 14b, and 15a, 15b are located between the support 3 and the rotator means 4. The signal transmitters 14a and 15a are connected to the support 3, while the other transmitters 14b and 15b are connected to the rotator means 4. Each pair of transmitters 14a and 14b (or 15a and 15b) are designed (as well known in the art) to send signals to each other without contacting each other. In addition, signals (for exciting the probes 10) transmitted from a flaw-detector circuit (not shown) are sent to the probes through the transmitters 14a and 14b, while inspection signals transmitted from the probes are sent to the flaw-detector circuit through the transmittens 15a and 15b. A means 18 for rotating the rotator means 4, such as a motor, is mounted on a base 17. A pulley 19 is connected to a drive shaft of the motor 18. A belt 20 is fitted onto the pulley 19 and the pulley 8 of the rotator means 4. Numerals 23, 22, and 21 designate tension rollers pressed against the belt 20, bars supporting the rollers 23, and means supporting the bars 22, respectively. The support bars 22 are urged from the support means 21 in directions indicated by arrows of FIG. 2. In the foregoing construction, when the motor 18 is operated, the rotator means 14 is rotated around the predetermined axis 11 of the material 7, thereby causing the probes 10 to revolve around the same axis 11. Then, the material 7 is passed into the cylindrical space 6 in such a manner that its axis is aligned with the predetermined one 11, and the circumference of the material is searched for flaws by the probes 10. Since the material is passed in its lengthwise direction, the inspection is made in a helical manner. The probes 10 may be revolved at a rate of, e.g., 20 to 80 r.p.s. Also, as a general rule, the material 7 is passed through the space 6 at a rate of 1 to 9 meters per second. Moreover, in usual cases the diameter of the material 7 is 20 m.m. or more. If the material 7 is warped at a certain portion thereof, its axis 7a is deviated from its predetermined one 11 while the warped portion is going through the space 6. For example, in such a case, the material axis 7a may deviate therefrom as indicated by the arrow X of FIG. 1. Thereupon, the amount of deviation is detected by one or more of the sensors 13 determining the variation of distance effected between the circumference of the material 7 and the sensor 13. Then, the sensor 13 transmits the deviation-detection signal to its associated cylinder-operating means (not shown), which causes the cylinder 2 to move its piston rod 2a so that the support 3 and rotator 4 shift their positions in the same direction and distance as the material, thus allowing their axes instantly to resume the coincidence with the deviated axis of the material. Accordingly, the center of revolution of the probes 10 is allowed to coincide with the material axis 7a at all times, so that the spaces between the probes 10 and the circumference of the material 7 are maintained constant in distance. In the event the material axis 7a has deviated as indicated in FIG. 1, the foregoing adjustment is made downward; however, such an adjustment does not cause the belt 20 to loosen, but the belt is maintained tight by the tension rollers 23 pressing against the belt.

If a portion of the material 7 is larger than its other portions, the cylinders 9 are operated to move their piston rods 9a backwards, when the larger portion is inspected, so that the same portion does not run against the probes 10.

Figure 3:
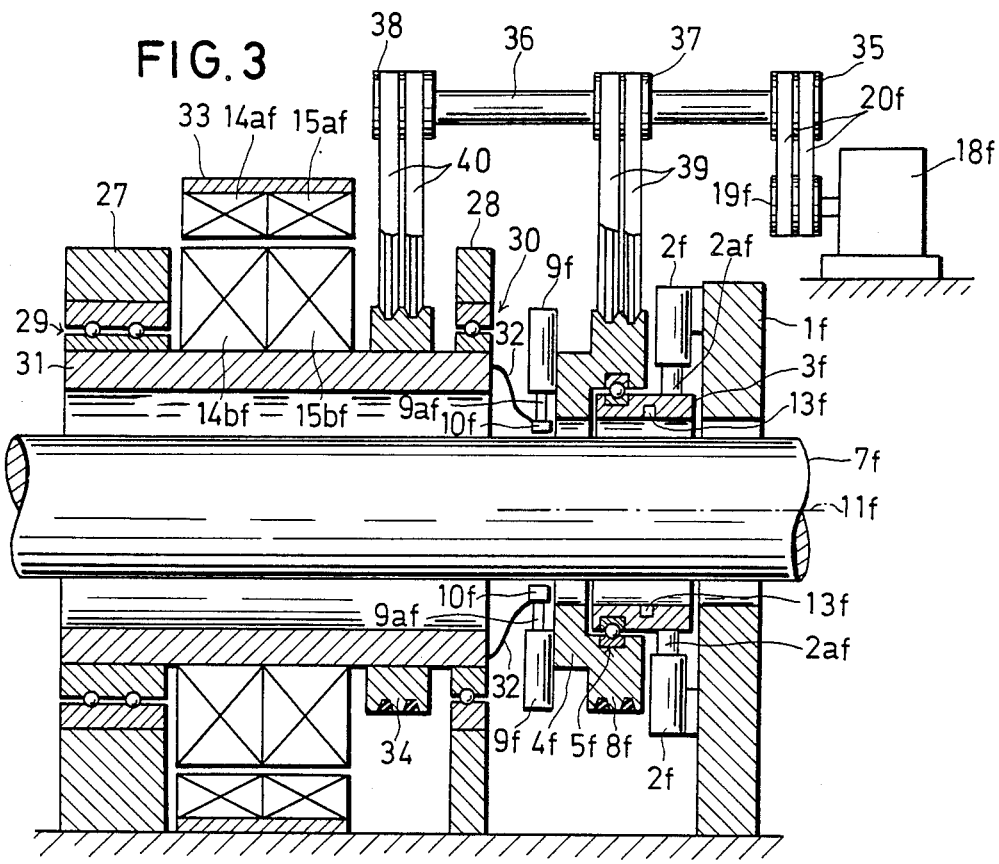
FIG. 3 is a vertical cross section of a second form of construction.

FIG. 3 illustrates another embodiment of the invention in which signal transmitters 14bf and 15bf are connected not to a rotator means 4f, but to another rotator means 31 which is movably (rotatably) connected to fixed frames 27 and 28 through bearings 29 and 30. The signal transmitters 14bf and 15bf are also connected to probes 10f by means of interconnection lines 32. On the other hand, signal transmitters 14af and 15af are connected to a fixed frame 33. Both rotator means 4f and 31 are rotated by an interlock mechanism including a driven shaft 36 with pulleys 35, 37, and 38. A drive belt 20f is fitted onto the pulleys 35 and 19f, and timing belts 39 and 40 are fitted onto the pulleys 37 and 8f and those 38 and 34, respectively. This interlock mechanism allows the rotator means 4f and 31 to rotate simultaneously when a motor 18f is operated. Although not shown, tension rollers are pressed against the timing belt 39 as in FIG. 2.

In the foregoing embodiment, the construction (including a support 3f, rotator means 4f, and the like) adapted to be moved perpendicularly to a predetermined axis 11f of a material 7f by a support cylinder 2f is of a smaller size than that of FIGS. 1 and 2; therefore, the central point of circular motion of the probes 10f can be made to follow the axis of the material 7f with better accuracy when the (actual) axis of the material is deviated from the predetermined axis 11f.

Figure 4:
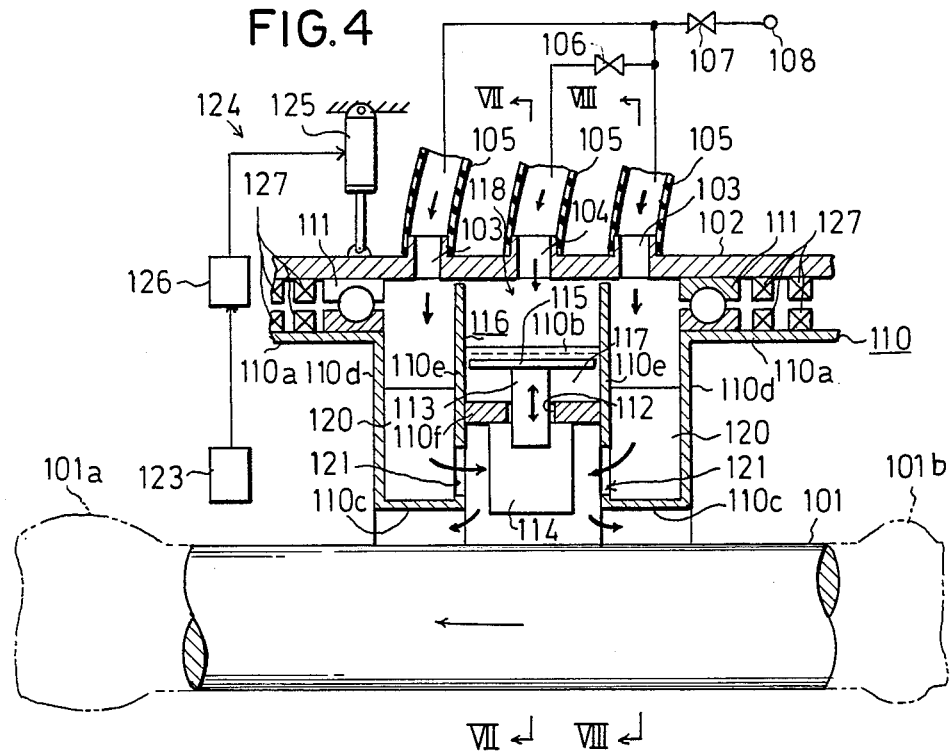
FIG. 4 is a vertical cross section of a third form of construction which shows only the upper half thereof.
Figure 5:
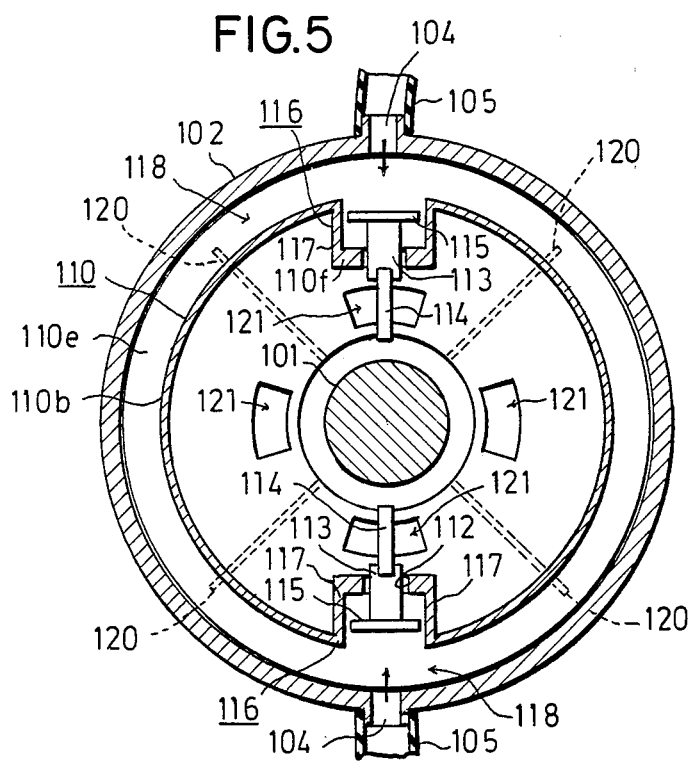
FIG. 5 is a reduced sectional view taken on the line VII—VII of FIG. 4.
Figure 6:
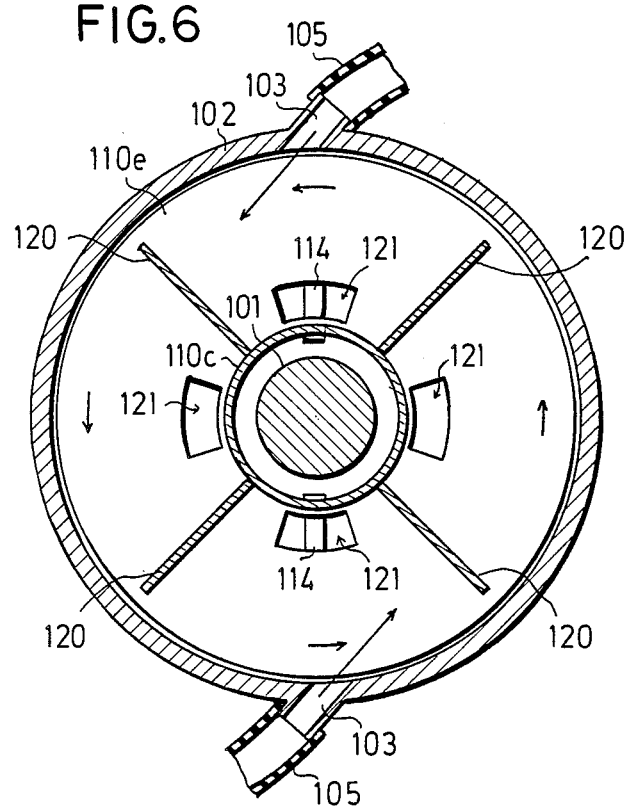
FIG. 6 is a reduced sectional view taken on the line VII—VII of FIG. 4.

FIGS. 4, 5, and 6 illustrate a still further flaw detector embodying the present invention. Numeral 101 designates a heated or cooled, rounded bar of steel or other kind of metal to be conveyed in a direction indicated by an arrow of FIG. 6 while being inspected for flaws.

This material 101 generally measures 25 to 80 millimeters in diameter, and has greater diameters at its both ends 101a and 101b. Numeral 102 designates a tubular support through which to pass the material 101. This same support 102 is supported (by a means not shown) movably in directions perpendicular to an axis of the material 101 predetermined through the cylindrical space of the support 102. The top and the bottom of the support 102 each are provided with a pair of air-blow openings 103 and an air-supply opening 104 located between the air-blow openings 103. These openings 103 and 104 are all connected to an air-supply source 108 (such as a compressor) through tubes 105 (such as flexible hoses) and valves 106 and 107. A rotator means 110 is movably (rotatably) connected to the inner side of the support 102 through bearings 111. The rotator means 110 comprises cylindrical sections 110a, 110b, and 110c, flange sections 10d and 10e, and a probe-installation section 10f which are all integrally formed with one another. The probe-installation section 10f has an opening 112 through which a probe support 113 is located movably in radial directions of the rotator means 110. To one end of the support 113 is connected a probe 114 for detecting flaws on the surface of the material 101. The probe 114 may be of an ultrasonic type, of an eddy-current type, or of any other suitable type. A plate 115 is attached to the other end of the support 113 at right angles thereto. Numeral 116 designates a wall which surrounds the range of movement of the plate 115 (which is effected when the plate 115 is subjected to elevated pressure as described hereafter). This wall 116 is formed of a portion of the flange sections 110e (of the rotator means 110) and side plates 117 fixed to the same section 110e, and is shaped into a box opened at its nearest side to the tubular body 102. In passing, the flaw-detector section comprising the foregoing probe 114 and its associated construction is not a single one in number, but there are provided two identical detector sections in all (as clearly shown in FIG. 5). Numeral 118 designates an annular space which is defined by the tubular body 102, the flange sections 10e, and the cylindrical section 11b and allows the air-supply openings 104 to communicate with the spaces surrounded by the walls 116. Numeral 120 designates blades which each are fixed to the flange sections 110d and 110e and the cylindrical section 110c. As shown in FIG. 6, four blades 120 are located between opposite flange sections 110d and 110e, and therefore, there are provided eight blades 120 in all. A pair of airflow openings 121 are provided between each probe 114. Also, additional two pairs of flow openings 121 are oppositely provided in a direction perpendicular to that in which the two pairs of flow openings 121 located between the probes 114 are opposed to each other. A plurality of sensors 123 are located around the predetermined passage of the material 101 and spaced apart from one another at equal intervals. The sensors 123 may be four in number, for example. As with the sensors 13 of FIG. 1, the function of each sensor 123 is to detect the actual axis of the material 101 deviating from its predetermined axis when the material is passed through the detector. In conjunction with each deviation sensor 123 is provided a mechanism 124 for displacing the tubular support 102 when the sensor 123 has detected a deviation of the material axis. The displacement mechanism 124 comprises a cylinder 125 for displacing the support 102 in directions perpendicular to the predetermined axis of the material and a means 126 for operating the cylinder 125 in accordance with a detection signal transmitted from the deviation sensor 123. As with the first embodiment, when a deviation of the material has been detected, the displacement mechanism 124 causes the support 102 to move in the same direction and distance as the deviation of the material axis, so that the center of rotation of the rotator means 110 follows the deviation to remain coincident with the actual axis of the material 101. Numeral 127 designates a number of annular signal-transmission coils. A half of the coils 127 are connected to the support 102 while the other coils 127 are connected to the rotator means 110, and each coil 127 connected to the support 102 and its opposing one to the means 110 make up a pair. The coils 127 are designed to transmit signals to activate the probes 14 (e.g., signals to excite the probes in case the probes are of an eddy-current type) from the support 102 to the rotator means 110, or transmit flaw-detection signals produced by the probes 114 from the rotator means 110 to the support 102. Instead of the signal-transmission coils 127, however, a wireless device (to be installed on the rotated means 110) may be employed for the same purpose. The foregoing flaw detector is operated as follows: The air-supply source 108 is operated and the valve 107 is opened to supply air (through the tubes 105) from the blow openings 103 into the spaces in which the blades 120 are located. The air thus supplied is virtually prevented from escaping from the foregoing spaces to the right-hand or left-hand side in FIG. 4 by the bearings 111 (separating foregoing spaces from the spaces between the support 102 and the cylindrical sections 110a of the rotator means 110) and the flange sections 110e (whose outward edges are in very close proximity to the inner side of the support 102). The air supplied runs against the blades 120 to rotate them, and flows out of the openings 121 and a portion of the air runs against the probe 114. The blades 120 rotated cause the rotator means 110 and, therefore, the probe 114 to rotate. The rotational speed may be controlled by adjusting the valve 107. Then, the material 101 to be inspected for flaws is passed into the detector thus operated. The material 101 of FIG. 4 has a larger diameter at its forward end 101a as mentioned before; however, there is no possibility of the larger portion 101a colliding with the probe 114 because the probe is being subjected to a centrifugal force produced by the rotation of the rotator means 110 so that the probe is pulled in a radial direction further away from the passage for the material (as shown in FIG. 4). After the material 101 is passed into the detector, the valve 106 is opened to supply air from the opening 104 into the space 118 communicating with the space surrounded by the wall 116. Therefore, the pressures in both spaces are increased to move the plate 115 toward the material 101, causing the probe 114 to move nearer to the circumference of the material 101. The distance of movement of the probe 114 may be controlled by adjusting the valve 106, e.g., in such a manner that the distance between the circumference of the material and the inward end of the probe 114 becomes a fraction of a millimeter to several millimeters. Although the probe 114 is rotating (or moving circularly) when the air is supplied from the opening 104, the probe is certainly moved toward the material 101 by the supply of air (wherever the probe is moving out of the opposite position to that of the opening 104) because the air, once supplied into the annular space 118, is certain to make the foregoing increased pressure to move the plate 115 toward the material 101 irrespective of the position of the plate 115 during rotation.

While thus rotating around the material 101 in a helical manner (as the material is in movement to the left-hand side in FIG. 4), the probe 114 detects a flaw on the circumference of the material and transmits the detection signal to a flaw-detector circuit (not shown). Even if the material is of an elevated temperature, the increase in temperature of the probe is compensated by the cooling effect of the air coming from the openings 121 so that the probe is protected from damage due to overheating. In addition, since the probe is thus cooled by the air that has been used to rotate the rotator means 110, this cooling method may be noted as contributive to the saving of energy.

In the foregoing flaw detector, the mechanism for rotating the rotator means 110 mainly consists of the blades 120 and the air-blow openings 103 so that the whole rotational construction is of a light weight; therefore, the rotational speed may be made higher. Moreover, since the whole weight of rotational construction and support 102 are also relatively light, the means for displacing them (according to a deviation of the material), such as the cylinders 125, may be of a smaller power.

Figure 7:
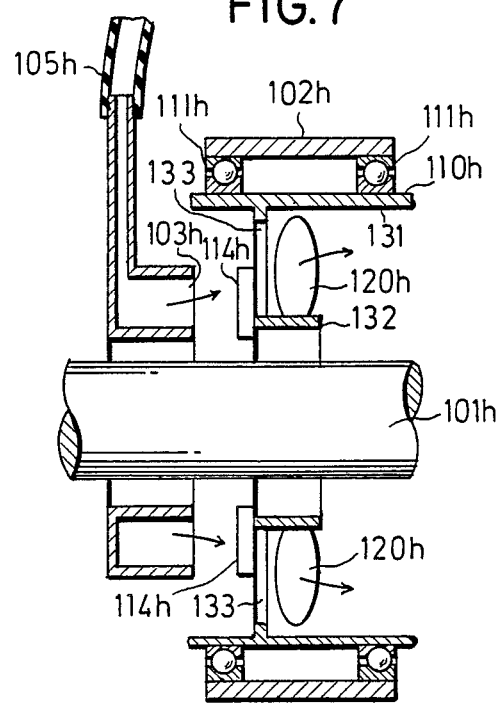
FIG. 7 is a partial view of a fourth form of construction.

FIG. 7 illustrates a detector construction similar to that of FIGS. 4, 5, and 6, but different in the method of using air. A rotator means 110h includes an outer tube 131 and an inner tube 132 connected to each other by an interconnection means 133. Probes 114h and blades 120h of twisted shape are attached to the inner tube 132. An annular air-blow opening 103h is so located as to surround a material 101h.

In this construction, air blown from the opening 103h first runs against the probe 114h to cool it and then against the blade 120h to rotate it so that the rotator means 110h is rotated around the material 101h.

Figure 8:
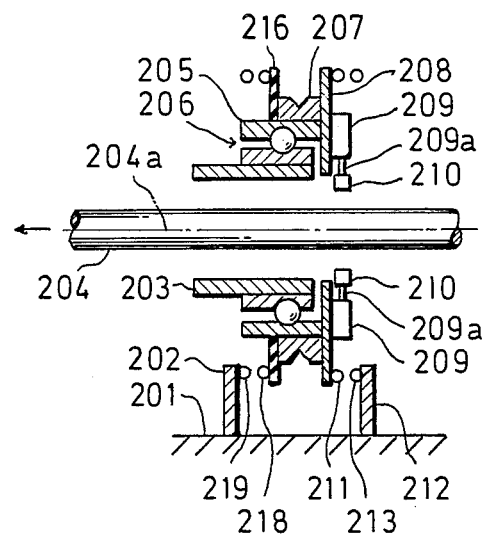
FIG. 8 is a vertical cross section of a fifth form of construction.
Figure 9:
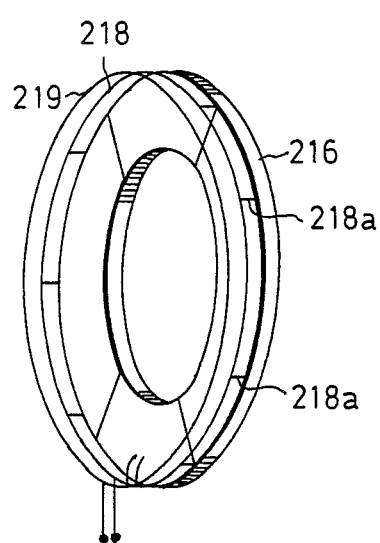
FIG. 9 is a perspective view of a substrate and its associated antennas used in the construction of FIG. 8.

The portions or sections of the embodiment of FIG. 7 functionally identical or equivalent to those of the embodiment of FIGS. 4, 5, and 8 are designated by the same numerals as the preceding ones and the alphabetical letter h attached thereto.

Figure 10:
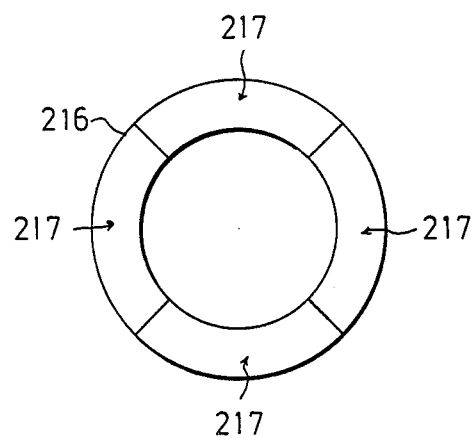
FIG. 10 is a front view of the substrate of FIG. 9.

FIGS. 10 to 13 illustrate a still further flaw detector embodying the present invention. As with the first embodiment (of FIGS. 1 to 2), a tubular support 203 is disposed movably in the directions perpendicular (or at right angles) to an axis 204a of a material 204 predetermined through the inner circular space of the support 203. Although not shown, there are provided a sensor means for detecting the actual axis of a material deviating from its predetermined axis 204a and a means for moving or displacing the support 203 in accordance with the detection of the sensor means. The material 204 to be inspected for flaws may be a steel bar in conveyance along a rolling line, or other material in other process. A cylindrical rotator means 205 is connected to the support 203 through bearings 206, and is rotatable with the predetermined axis 204a or deviated axis of the material as the rotational center. Numeral 207 designates a pulley connected to a rotation device (not shown) by means of a belt (not shown) so that the pulley causes the rotator means 205 to rotate when operated by the rotation device. Four cylinders 209 are connected to the rotator means 205 by means of a circular installation plate 208, and are equally spaced apart from one another at angles of 90° and with the rotational center of the rotator means 205 as the center in (circular) arrangement. The cylinders 209 each have a piston rod 209a which is provided with a probe 210 at its inward end. The piston rod 209a is moved forward or backward according to the diameter of the material 204 so that the probe 210 comes to the optimum position for detecting flaws on the circumference of the material. Although the probe 210 is one for the detection of flaws by eddy currents in the embodiment herein, it may be of any other suitable type. Numeral 211 designates a circular antenna connected to the installation plate 208 along its circumference. The antenna 211 is designed to receive driving (or exciting) signals from another circular antenna 213 which is located in conjunction with the antenna 211 and connected to a support means 202 fixed onto a floor 201 (although the antenna 213 may be disposed at any place other than indicated in FIG. 10, from which high-frequency signals can be transmitted to the receiving antenna 211). Opposite to the installation plate 208, a circular substrate 216 is attached to the rotator means 205. A printed circuit is used as the substrate 216 in the embodiment herein. As shown in FIG. 10, the substrate 216 is provided with four sets of circuits 217 for transmission of signals (having searched the material for flaws) in conjunction with the four probes 210. A circular antenna 218 is connected to the substrate 216 along its circumference and by support means 218a. The antenna 218 is designed to transmit signals corresponding to the foregoing signals having searched the material (the corresponding signals may be hereafter called "material-search transmission signal) to another circular antenna 219 which is located in conjunction with the antenna 218 and connected to a support means 202 fixed onto the floor 201 (although the antenna 219 may be disposed at any place other than indicated in FIG. 8, in which the signals from the transmission antenna 218 can be received).

Figure 11:
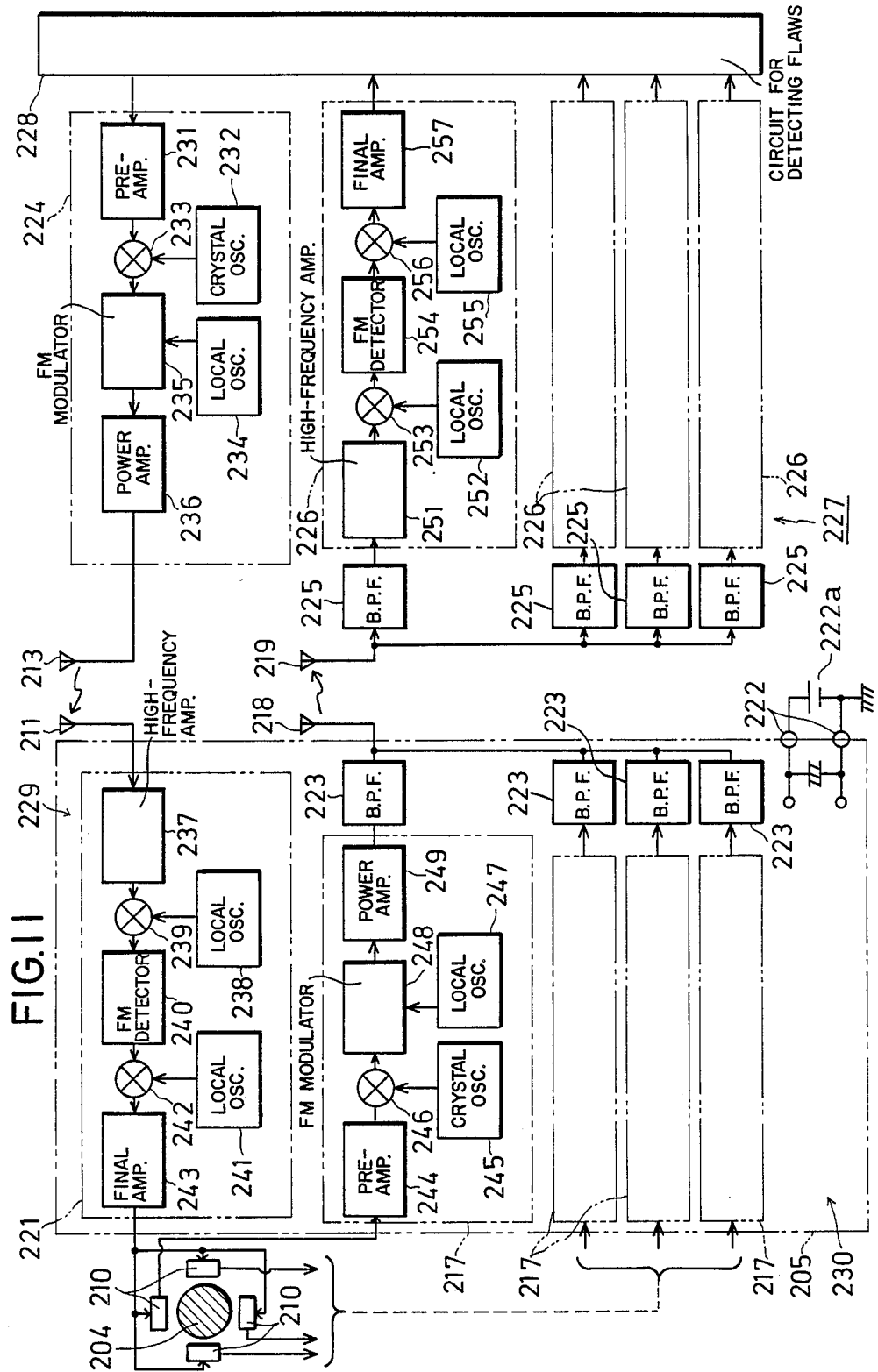
FIG. 11 is a block diagram of arrangement of signal-transmission circuits employed in the construction of FIG. 8.

Referring to FIG. 11, the rotator means 205 is also provided with a circuit 221 for receiving driving signals although the same circuit 221 is not shown in FIG. 8. In addition, a pair of slip rings 222 (not shown in FIG. 8) are installed onto the rotator means 205. The slip rings 222 are designed to supply power from a power-supply source 222a through feeder means connected to the support 203 and to the transmission circuit 217 or receiving circuit 221 as mentioned before so that those circuits are activated. Numeral 223 designates a number of bandpass filters which are different from one another in the range of frequencies so that each filter 223 allows only output signals from the transmission circuit 217 associated therwith to pass therethrough. The bandpass filters 223 are all provided on the circular (or annular) substrate 216. Numeral 224 designates a circuit for transmitting driving signals. Numeral 225 also designates a number of band-pass filters having the similar functions as the preceding ones 223. Numeral 226 designates receiving circuits. The receiving antenna 219, band-pass filters 225, receiving circuit 226 and the like constitute a receiver 227. Numeral 228 designates a circuit for detecting flaws by eddy currents which is well known in the art. In passing, the whole means indicated by numerals 211 and 221 and those indicated by 217, 218, and 223 may be referred to as "driving-signals supply section" 229 and "search-signals receiving section" 230, respectively, in this specification.

In the foregoing flaw-detector construction of FIGS. 8 to 11, the material 204 is moved at a rate of several meters to several tens of meters per second in a direction indicated in FIG. 8. The rotator means 205 is rotated at a rate of, for example, 1,800 r.p.m., thus allowing the probes 210 to inspect the material for flaws in a helical manner. Referring to FIG. 11, a description will be next made of the process of supply of a driving signal to the probes and transmission thereof after inspection: The circuit 228 (for detection of flaws by eddy currents) outputs a signal of 128 kHz (although the frequency of the signal may be lower or higher; for example, it may be 256 kHz). The signal is amplified at a pre-amplifier 231, and then at a mixer 233 is mixed with another signal of 100 kHz sent from a crystal oscillator 232, so that a signal of 28 kHz is produced. At a FM modulator 235 the new signal is modulated by a carrier wave of 400 MHz from a local oscillator 234, and amplified at a power amplifier 236. The amplified signal is transmitted from the antenna 213 to its associated one 211 as a driving-transmission signal. The signal is then amplified at a high-frequency amplifier 237, and at a mixer 239 is mixed with another signal of 390 MHz from a local oscillator 238, thus producing an intermediate-frequency signal of 10 MHz. The new signal is demodulated at a FM detector 240, and at a mixer 242 is mixed with another signal of 100 kHz from a local oscillator 241, so that a driving signal of 128 kHz is produced. The driving signal is amplified at a final amplifier 243, and sent to the probes 210 to excite them. The output signal of 128 kHz from the probe 210 may or may not detect a flaw on the material, and is amplified at a preamplifier 244. At a mixer 246 the amplified signal is mixed with a signal of 100 kHz sent from a crystal oscillator 245, producing a signal of 28 kHz. At a FM modulator 248 the new signal is modulated by a carrier signal from a local oscillator 247. The frequency of oscillations established by the local oscillator 247 for a particular transmission circuit 217 (or for a particular channel) is made different from those of oscillations established by the other local oscillators 247 (in the other transmission circuits 217) so that the frequencies of oscillations established by the four oscillators 247 are slightly different from one another; in addition, those frequencies are made slightly different from that of oscillations established by the local oscillator 234 of the transmission circuit 224(so that the frencuencies are not jammed). The frequency of oscillations established by each local oscillator 247 is 400 MHz or thereabouts (hereinafter referred to as "approximately 400 MHz"). The output signal of approximately 400 MHz from the FM modulator is amplified at a power amplifier 249, passes the band-pass filter 223, and is transmitted from the antenna 218 to its associated antenna 219 as a material-search transmission signal. The signals in the other channels also are all transmitted from one and the same antenna 218 to the other antenna 219.

The signal received by the antenna 219 then passes the bandpass filter 225, and is amplified at a high-frequency amplifier 251. At a mixer 253 the amplified signal (of approximately 400 MHz) is mixed with a signal of 390 MHz sent from a local oscillator 252 (though the signal from each local oscillator 252 in each receiving circuit 226 is made different from the other signals from the other three oscillators 252, as in the transmission circuits 217), so that an intermediate-frequency signal of 10 MHz is produced. The new signal is demodulated at a FM detector 254 so that it becomes a signal of 28 kHz. At a mixer 256 the signal is then mixed with a signal of 100 kHz sent from a local oscillator 255, producing a signal of 128 kHz (search-result signal). This signal is amplified at a final amplifier 257, and transmitted to the detector circuit 228. Having thus emitted the driving signal and received the searchresult signal, the detector circuit 228 determines whether the signal has detected a flaw on the material (as is well known in the art). Although the carrier waves have been described as having a frequency of approximately 400 MHz, they may be of any other frequency which makes wireless transmission possible: (e.g., may be in a range of 100 to 400 MHz). In addition, the number of the channels (or that of the probes) may be more or less than 4.

The foregoing technique of transmitting the driving signal and the search-result signal (through the stationary body of the detector construction and its rotating body) by high-frequency radio provides the advantage that the whole rotatable body may be made a lighter construction than those of the preceding embodiments which use coils to transmit the signals. The rotatable body lighter in weight can be rotated at a higher rate. With the rotational speed thus increased, the probes 210 may cover a larger area on the circumference of the material in search if the material is passed through the detector at the conventional velocity. Also, the material may be searched for flaws in a shorter period of time if the velocity of movement of the material as well as the rotational speed of the rotatable body is increased so as to keep the area covered by the probes unchanged.

Moreover, in the detector construction where the signals are transmitted in high-frequency radio, its rotatable body may reduced in its dimension in the direction of passage of the material; if the rotatable body is made such a smaller-sized one, the whole detector construction may be disposed in a relatively small place, e.g., between a finish rolling apparatus and a shearing device arranged along a rolling line.

Figure 12:
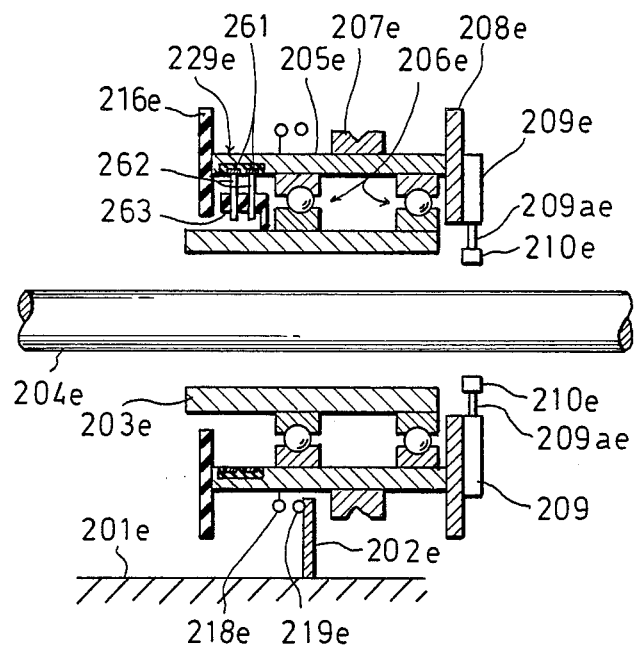
FIG. 12 is a vertical cross section of an sixth form of construction.

Referring to FIG. 12, the detector construction may be modified by constructing the driving-signal supply section of slip rings: Numeral 229e designates a driving-signal supply section which comprises slip rings 261 connected to a rotator means 205e with insulators provided therebetween. Numeral 262 designates electrodes of the slip rings 261 which are connected to a support 203e by a bracket 263 and slidably contact the slip rings 261. In this construction, a driving signal from the detector circuit is transmitted to probes 210e through the electrodes 262 and the slip rings 261. The portions or sections of the embodiment of FIG. 12 functionally idendical or equivalent to those of the embodiment of FIGS. 8 to 11 are designated by the same numeral as the preceding ones and the alphabetical letter e attached thereto. (Also, the equivalent portions of the embodiments that will follow hereafter are designated in the same manner, but with different alphabetical letters attached.)

Figure 13:
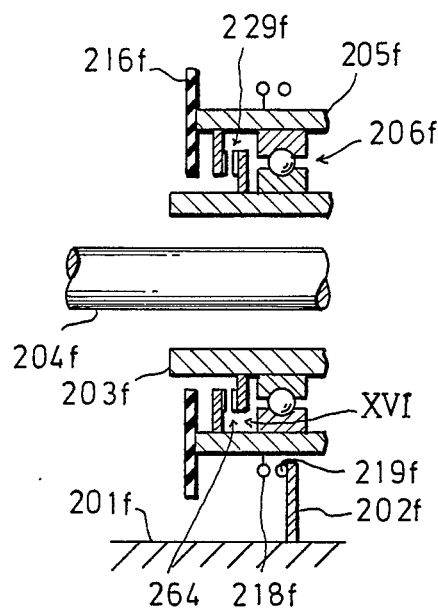
FIG. 13 is a partial, vertical cross section of a seventh form of construction.
Figure 14:
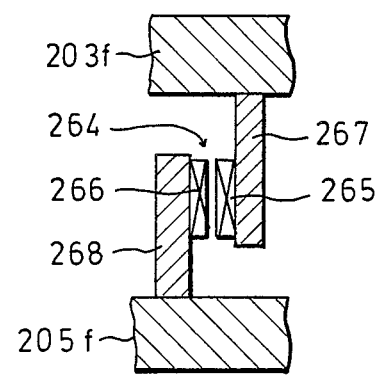
FIG. 14 is an enlarged view of the portion of the construction of FIG. 13 indicated by the arrow XVI.
Figure 17:
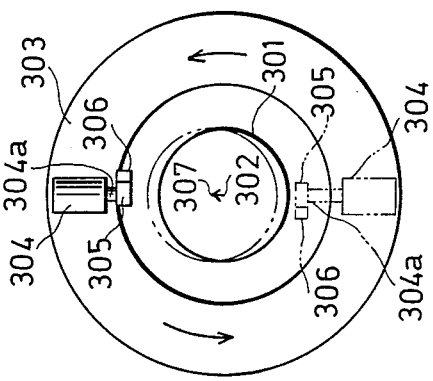
FIG. 17 illustrates the conventional detector construction with a probe searching a material for flaws.

Referring to FIGS. 13 and 14, the detector construction of FIG. 12 may be modified by constructing the driving-signal supply section of a pair of coils: Numerals 265 and 266 designate a signal-transmission coil and a signal-receiving coil, respectively, which are opposed to each other so that driving signals are transmitted from the former coil 265 to the latter 266. The transmission coil 265 is connected to a support 203f by means of a bracket 267, while the receiving coil 266 is connected to a rotator means 205f by means of a bracket 268.

Figure 15:
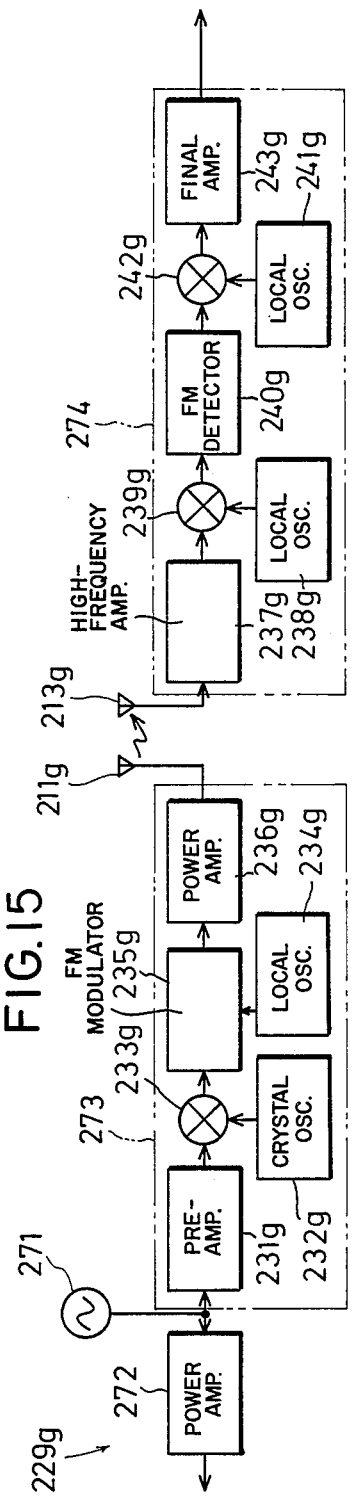
FIG. 15 illustrates a partial modification of the arrangement of signal-transmission circuits of FIG. 11.

Referring to FIG. 15, the detector construction of FIGS. 8 to 11 also may be modified by providing an oscillation circuit for emitting driving signals as a component of the driving-signal supply section: Numeral 271, 272, and 273 designate an oscillation circuit to emit driving signals, a power amplifier, and a transmission circuit, respectively. The oscillation circuit 271 is located in the vicinity of the rotator means. The transmission circuit 273 is of the same construction as that 224 of FIG. 11. The entire means collectively indicated by numerals 271, 272, and 273 takes the place of the receiving circuit 221 of FIG. 11. In addition, numeral 274 designates a receiving circuit which is of the same construction as that 221 of FIG. 11 and takes the place of the transmission circuit 224 of FIG. 11. In the foregoing construction, the oscillation circuit 271 emits a driving signal of 128 kHz. The signal is amplified at the power amplifier 272, and transmitted to the probes while part of the signal is simultaneously sent to an antenna 211g through the transmission circuit 273 and received by an antenna 213g. The signal, as a reference signal, is then transmitted to the detector circuit 228 (of FIG. 11) through the receiving circuit 274.

Figure 16:
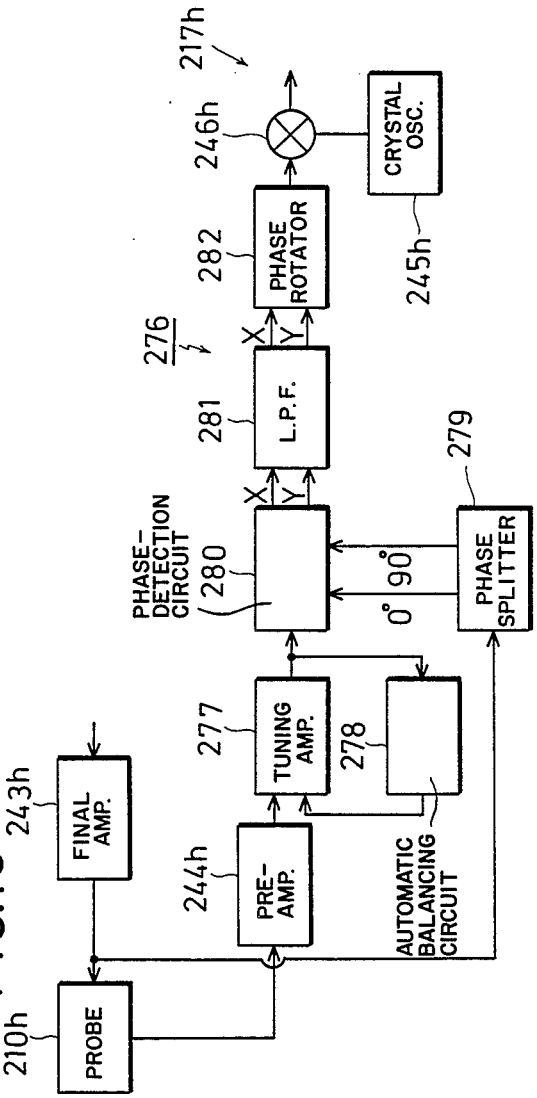
FIG. 16 illustrates another partial modification of the arrangement of signal-transmission circuits of FIG. 11.

Referring to FIG. 16, the detector construction of FIGS. 10 to 11 may be further modified by providing an additional circuit in the signal-transmission arrangement; that is, a transmission circuit 217h may be provided with a signal-processor circuit 276 (or, a circuit for sorting out the signals having detected flaws) at its input side. The signal-processor circuit 276 comprises a number of means 277 to 282 that will follow: In this construction, the signal from the probe 210h (having searched the material for flaws) is amplified at a pre-amplifier 244h, and then amplified by entering a tuning amplifier 277 from one input end thereof. The amplified signal is also sent to an automatic balancing circuit 278. This circuit 278 emits a signal to another input end of the tuning amplifier 277 in order to make the signal amplified therein 0 (zero). It is to be noted that, however, the time constant of automatic balancing operation of the circuit 278 is practically set so that the circuit 278 does not respond to a defective signal (i.e., a signal having detected a flaw on the material). With the time constant thus set, the output of the tuning amplifier 277 is kept at 0 when the signal received thereby is not a defective one, but produces an output signal when the signal received is a defective one. On the other hand, part of an output signal (driving signal) from a final amplifier 243h is transmitted to a phase splitter 279 as a reference signal. The splitter produces a signal different from the reference signal by a phase angle of 90°, and the signal produced (90° signal) is transmitted to a phase-detection circuit 280 together with the reference signal (0° signal). With reference to the 0° and 90° signals, the phase-detection circuit 280 takes a 0°-direction signal (X-signal) and a 90°-direction signal (Y-signal) from the output signal from the tuning amplifier 277. The signals taken are allowed to pass a low-pass filter 281 so that the higher frequencies are removed therefrom. The signals are then sent to a phase rotator 282, where both X-signal and Y-signal are rotated at an angle of $\phi$ in order to have the maximum S/N. X-signal ($\chi$) and Y-signal ($\psi$) thus rotated is formulated as follows:

$$\chi = X \cos \phi - Y \sin \phi,$$

$$\psi = X \sin \phi + Y \cos \phi$$

It may be seen that the S/N ratio is increased by setting the value $\phi$ so that the noise signal, such as $\chi$ signal, becomes 0 (X cos $\phi$ = Y sin $\phi$) and taking out $\psi$ signal only. The output signal from the phase rotator 282 is made into a transmission signal at a transmission circuit 217h (as in FIG. 11), and then transmitted to the transmission antenna. It is to be added that once the signals are output from the phase-detection circuit 280, the signal frequencies thereafter do not become no more than 1 kHz. Also, the mere information of amplitude is quite enough for the operation, thus making wireless transmission very easy. Furthermore, in the embodiment herein, since two channels are required for the wireless transmission of signals immediately after phase detection (by 280), formal transmission is made after phase rotation (by 282), i.e., when only a single channel has become required for transmission.

As described above, the output signal from the signal-processor circuit 276 is of relatively low frequencies and requires no stabilization of its phase. By incorporating such a circuit 276 into the rotatable body of the detector, therefore, none of the circuit 217 for transmitting the flaw-search signal (or one having made a search), the circuit for receiving the same signal, or the like calls for a higher degree of accuracy which would otherwise be required of them. Hence these other circuits may be made simpler in construction. (With the construction not including the processor circuit 276, the receiver having received the search signal is required to make the same processing of the signal as described above. In such a case, the processor circuit which would be included in the receiver and have a phasedetection circuit is required to stabilize the phase of the signal within an accuracy of ±5°, thus making necessary the use of wireless-transmission circuits and reveiving circuits with higher degrees of accuracy.)

Any of the foregoing techniques of wireless transmission of a driving signal from the detector circuit and a search-result signal to the detector circuit with high-frequency carrier waves may be applied to the detector constructions of FIGS. 4 to 7: for example, the construction of FIG. 4 may be modified by removing the coils 127 therefrom, providing its rotator means 110 with the sections 229 and 230 of FIG. 11, and disposing the arrangement as collectively indicated by numerals 213, 224, 228, 219, 225, and 226 of FIG. 11 in the vicinity of the construction of FIG. 4. As many apparently widely different embodiments of this invention may be made without departing from the spirit and scope thereof, it is to be understood that the invention is not limited to the specific embodiments thereof except as defined in the appended claims.

What is claimed is:

1. A flaw detector comprising:
    (a) a framework disposed by the side of a predetermined axis of a meterial to be inspected for flaws;
    (b) means mounting a support on said framework for movement in a plurality of directions perpendicular to said predetermined axis of the material;
    (c) a rotator means rotatably mounted on said support in such a manner as to rotate around the axis of the material while the material is passed along said predetermined axis;
    (d) means for rotating said rotator means;
    (e) a plurality of probes mounted on the rotator means and spaced from the material to be inspected for inspecting the circumference of the material for flaws;
    (f) a plurality of means spaced equally about said predetermined axis for detecting the amount and direction of deviation of the actual axis of the material from said predetermined axis which may occur while the material is being passed along said predetermined axis; and (g) mechanisms located respectively at the same angular position around said predetermined axis as each said deviation-detecting means for shifting said support in said direction in accordance with the amount of deviation of the material detected by said means so that said rotator means shifts its position simultaneously in the same direction and amount as said support in order for its rotational center to remain coincident with the actual axis of the material.

2. A flaw detector in accordance with claim 1 wherein said deviation-detecting means comprises a sensor connected to said support for determining the distance between the material and said sensor so as to detect variations in said distance from the one predetermined on the basis of said predetermined axis of the material and said shift mechanism comprises a cylinder connected at one end to said framework and having a piston rod connected to said support at its other end and a means for operating said cylinder in accordance with the amount of variation in said distance which represents the amount of deviation of the material from said predetermined axis thereof.

3. A flaw detector in accordance with claim 1 wherein said means for rotating said rotator means includes blades connected to said rotator means and openings located in the proximity of said blades for blowing air against said blades so as to rotate said rotator means.

4. A flaw detector in accordance with claim 3 wherein said rotator means is provided with passages through which said air blown against said blades is allowed to flow toward said probes.

5. A flaw detector in accordance with claim 3 characterized in that:
(a) said rotator means is provided with a support rod which extends along the radial direction of said rotator means and is movable along said direction;
(b) said each probe is connected to the end of said support rod which is closer to the rotational center of said support means;
(c) a plate is connected to the other end of said support rod at right angles thereto so as to move said support rod toward the material being passed into said cylindrical space;
(d) said rotator means is further provided with an enclosure defining a space within which said plate is allowed to move in the radial directions of said rotator means and having a bottom which is provided with an opening to allow said support rod to move therethrough; and
(e) said support is provided with an opening communicating with said space defined by said enclosure so as to supply air into said space so that said plate is pressurized and moved toward the material, thus moving said support rod toward the same direction; and
(f) an annular air passage is provided along the inner side of said support so that said air-supply opening of said support remains communicating with said space defined by said enclosure wherever said enclosure is positioned while being revolved by the rotation of said rotator means.

6. A flaw detector in accordance with claim 1 wherein said rotator means is provided with transmission circuits for modulating signals from said probes having searched the material for flaws with high-frequency carrier waves so as to produce transmission signals corresponding to said signals made the search and an antenna is provided in conjunction with said transmission circuits for emitting said transmission signals into space.

7. A flaw detector in accordance with claim 6 further including an antenna for receiving a driving-transmission signal transmitted thereto in a wireless manner and a circuit for taking a driving signal from said driving-transmission signal and transmitting said driving signal to said probes.

8. A flaw detector in accordance with claim 6 further including a circuit provided between said probe and said transmission circuit so as to receive said signals from said probe and sort out the signals having detected flaws from those having detected no flaws and output the former signals only.

* * * * *